United States Patent [19]

Hanson

[11] Patent Number: 4,522,823

[45] Date of Patent: Jun. 11, 1985

[54] OREXIGENIC USE OF α-FLUOROMETHYL-HISTIDINE

[75] Inventor: Harley M. Hanson, Norristown, Pa.

[73] Assignee: Merck & Co., Inc., Rahway, N.J.

[21] Appl. No.: 568,451

[22] Filed: Jan. 5, 1984

[51] Int. Cl.$^3$ ............................................ A61K 31/415
[52] U.S. Cl. ..................................................... 514/400
[58] Field of Search ..................................... 424/273 R

[56] References Cited

U.S. PATENT DOCUMENTS 4,325,961  4/1982  Kollanitsch et al. ........... 424/273 R Primary Examiner—Albert T. Meyers
Assistant Examiner—John M. Kilcoyne
Attorney, Agent, or Firm—Gabriel Lopez; Hesna J. Pfeiffer

[57] ABSTRACT

α-Fluoromethyl-histidine is used to increase food intake.

3 Claims, No Drawings

OREXIGENIC USE OF α-FLUOROMETHYL-HISTIDINE

BACKGROUND OF THE INVENTION

α-Fluoromethyl-histidine is described in U.S. Pat. No. 4,325,961. It is described therein as being a decarboxylase inhibitor and useful in the prevention of gastric lesions and in treating allergic conditions.

SUMMARY OF THE INVENTION

It has now been found that α-fluoromethyl-histidine (α-FMH) is useful as an orexigenic agent; i.e., it will increase appetite and food intake in man and animals.

DETAILED DESCRIPTION OF THE INVENTION

The invention comprises a method of stimulating appetite comprising administering to humans or animals an effective appetite-stimulating amount of α-FMH or a pharmaceutically acceptable salt thereof. The appetite-stimulating effects of α-FMH administration are of long duration; i.e., significant increases in food intake have been observed 26 hours after administration.

The compound active in the methods of the present invention is of the formula:

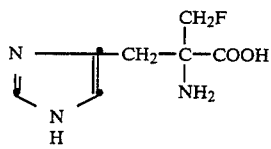

and the pharmaceutically acceptable salts thereof. In general, the salts are those of the formula I base with a suitable organic or inorganic acid. Preferred inorganic acid salts are the hydrohalides e.g. hydrochlorides, hydroiodides, hydrobromides; the sulfates, and the phosphates. The hydrohalides, and especially the hydrochlorides, are more preferred.

The formula I compounds have a chiral center and may occur in optically active forms i.e., as optical isomers. These isomers are designated conventionally by the symbols L and D, + and −, l and d, S and R or combinations thereof. Where the compound name or formula has no isomer designation, the name or formula includes the individual isomer, mixtures thereof, and racemates.

The compounds having the S-isomer configuration are, in general, preferred.

In the method of treatment of the present invention it is noted that the precise unit dosage form and dosage level depend upon the case history of the individual being treated and consequently are left to the discretion of the therapist. In general, however, the compound described above produce the desired effect of appetite stimulation when given at from about 1 to about 25 mg per kg body weight per day. The preferred form of delivery of the instant compounds for appetite stimulation of domestic animals is by solution in drinking water or preformulated feedstuffs. For human and animal administration, any of the usual pharmaceutical oral forms may be employed such as tablets, elixirs and aqueous suspensions comprising from about 1 to about 25 mg of the compounds of this invention per kg body weight given daily. Thus, for example, tablets given 1-3 times per day comprising from about 0.25 to about 25 mg of the compounds of this invention are suitable for human treatment. Sterile solutions (representatively given for human treatment) for injection comprising from about 0.25 to about 25 mg of the compounds of this invention given 1 to 3 times daily are also suitable means of delivery.

EXAMPLE 1

EFFECTS OF α-FMH ON FOOD INTAKE OF CATS OVER A 2-HOUR PERIOD

Twenty male cats that had been housed in the laboratory for more than 6 months were randomly assigned to one of two treatment groups. All animals had been fed a surplus of a commercially available wet canned food at the same time daily for the preceding month; any uneaten food was routinely removed after 2 hours. On Day 1 of the study the amount of food eaten was determined after 30, 60 and 120 minutes of the feeding period. On Day 2 the same procedure was followed except all cats were dosed with water orally 2 hours preceding feeding. On Day 3 group I was dosed with water, and group II with α-FMH, 25 mg/kg p.o. Day 4 was a repeat of Day 2 and Day 5 was similar to Day 1.

The average amounts of food eaten by the two groups for Days 2, 3 and 4 of the study are shown in Table 1-1. These data show that at a dose of 25 mg/kg p.o., α-FMH significantly increased the amount of food eaten.

TABLE 1-1

FOOD EATEN BY GROUPS OF CATS TREATED WITH α-FMH PRECEDING A 2-HOUR FEEDING PERIOD

| Group | Treatment | Day 2 (gm) | Day 3 (gm) | Day 4 (gm) |
|---|---|---|---|---|
| I | Control, H₂O | 149 | 159.89 | 173.69 |
| II | α-FMH, 25.0 mg/kg | 205.00 | 254.39 | 223.69 |

EXAMPLE 2

EFFECTS OF α-FMH ON FOOD INTAKE OF CATS OVER A 26-HOUR PERIOD

Male cats were fed a surplus of a commercially available canned food at the same time daily; any uneaten food was removed after two hours. The amount of food eaten on a particular day was determined by weighing the food offered (approximately 420 gm) before and after the feeding period. Water was available at all times. Compounds were administered by gavage dissolved in water.

To determine the effects of various doses of α-FMH, the cats were randomly assigned to groups of 7–10 animals and administered various doses of α-FMH or water two hours preceding feeding. As a control, all cats were dosed with water two hours preceding feeding on the preceding day.

To see if α-FMH was active over a longer period of time, the preceding procedure was followed, except that the cats were dosed 4, 6, 17, and 26 hours preceding testing. In the 26 hour study, food consumption was recorded during the two days preceding and following testing.

α-FMH significantly increased the amount of food eaten over a dose range of 3.125 to 25 mg/kg p.o. Since the data gathered showed marked day-to-day variability and in many cases the control groups ate less food on Day 2 than Day 1, and to allow comparisons and include all the data, the data were expressed as (grams food eaten on Day 2—grams food eaten on Day 1)+100 preceding analysis. The percent change in food eaten compared to the concurrent control group is shown in Table 2-1.

TABLE 2-1
EFFECTS OF α-FMH ON FOOD INTAKE OF CATS

| Dose of α-FMH mg/kg p.o. | No. of Cats | % Change from Control Group |
|---|---|---|
| 1.5625 | 8 | 17.76 |
| 3.125 | 7 | 56.79 |
| 6.25 | 7 | 60.07 |
| 6.25 | 8 | 58.04 |
| 12.5 | 8 | 59.39 |
| 25 | 10 | 33.4 |

A dose of 6.25 mg/kg/p.o. was used for duration of action studies. This dose of α-FMH given 4 and 6 hours preceding feeding significantly increased the amount of food eaten on Day 2 compared with Day 1. In a study with 22 cats, α-FMH, 6.25 mg/kg p.o., administered 17 hours pretest, significantly increased the amount of food eaten compared to the control.

The data collected following dosing 26 hours preceding the test meal are shown in Table 2-2. The average grams food eaten in two hours for five days are shown. Water was administered 2 hours preceding feeding on Day 2. Treatments were given 2 hours preceding feeding on Day 3. α-FMH significantly increased the amount of food eaten 2 and 26 hours after dosing.

At no time at any dose or time were any overt signs of CNS activity noted in the treated cats.

TABLE 2-2
EFFECTS OF α-FMH ON FOOD INTAKE OF CATS

| Treatment | Days | | | | |
|---|---|---|---|---|---|
|  | 1 | 2 | 3 | 4 | 5 |
| Control | 146.86 | 148.08 | 132.95 | 136.26 | 134.47 |
| α-FMH 6.25 mg/kg p.o. | 153.86 | 138.65 | 184.73 | 162.39 | 154.82 |

TABLE 2-2-continued
EFFECTS OF α-FMH ON FOOD INTAKE OF CATS

| Treatment | Days | | | | |
|---|---|---|---|---|---|
|  | 1 | 2 | 3 | 4 | 5 |
| kg p.o. | | | | | |

EXAMPLE 3

EFFECTS OF α-FMH ON FOOD INTAKE OF CATS

Cats that had been fed a commercially available wet cat food at the same time daily were used for the study. Two hours preceding a two-hour feeding period, the cats were given one of 3 treatments: water, α-FMH (0.7813 mg/kg p.o.), or α-FMH (1.5625 mg/kg p.o.). The amount of food eaten was determined by weighing the offered food (approximately 420 grams) before and after the feeding period.

The data collected, expressed as means, is shown in Table 3-1. α-FMH at both dosages produced significantly increased food intake.

TABLE 3-1
EFFECTS ON FOOD INTAKE IN CATS

| Treatment | Dose (mg/kg p.o.) | Grams Eaten | Change from Control |
|---|---|---|---|
| Water |  | 139.18 ± 48.3 | — |
| α-FMH | 0.7813 | 165.31 ± 40.4 | 19% |
| α-FMH | 1.5625 | 181.86 ± 39.9 | 31% |

What is claimed is:

1. A method of stimulating appetite comprising administering orally or by sterile injection to man or animal in need of such treatment an effective appetite stimulating amount of α-fluoromethylhistidine or a pharmaceutically acceptable salt thereof.

2. A method of claim 1 wherein said amount is 1 to 25 mg/kg body weight.

3. A method of claim 1 which comprises administering 1–3 times per day an effective appetite stimulating amount of α-fluoromethylhistidine or a pharmaceutically acceptable salt thereof.

* * * * *